US012734001B2

(12) United States Patent
Tschudy et al.

(10) Patent No.: US 12,734,001 B2
(45) Date of Patent: Sep. 15, 2026

(54) END EFFECTOR DRIVE MECHANISMS FOR SURGICAL INSTRUMENTS SUCH AS FOR USE IN ROBOTIC SURGICAL SYSTEMS

(71) Applicant: Covidien LP, Mansfield, MA (US)

(72) Inventors: Christopher T. Tschudy, Arvada, CO (US); Dylan R. Kingsley, Broomfield, CO (US); Sara A. Malang, Longmont, CO (US); James H. Bodmer, Longmont, CO (US); Tony G. Moua, Broomfield, CO (US); Andrew W. Zeccola, Allston, MA (US); Curtis M. Siebenaller, Frederick, CO (US); Haralambos P. Apostolopoulos, Highlands Ranch, CO (US); Russell W. Holbrook, Longmont, CO (US); William R. Whitney, Boulder, CO (US); Jason G. Weihe, Boulder, CO (US); Zachary S. Heiliger, Nederland, CO (US)

(73) Assignee: Covidien LP, Mansfield, MA (US)

( * ) Notice: Subject to any disclaimer, the term of this patent is extended or adjusted under 35 U.S.C. 154(b) by 788 days.

(21) Appl. No.: 17/403,508

(22) Filed: Aug. 16, 2021

(65) Prior Publication Data

US 2023/0046473 A1 Feb. 16, 2023

(51) Int. Cl.
*A61B 34/35* (2016.01)
*A61B 18/14* (2006.01)

(52) U.S. Cl.
CPC .......... *A61B 34/35* (2016.02); *A61B 18/1445* (2013.01); *A61B 2562/0257* (2013.01); *A61B 2562/0261* (2013.01)

(58) Field of Classification Search
CPC ................ A61B 34/35; A61B 18/1445; A61B 2562/0257; A61B 2562/0261;
(Continued)

(56) References Cited

U.S. PATENT DOCUMENTS 5,752,973 A 5/1998 Kieturakis
5,792,135 A 8/1998 Madhani et al.
(Continued)

FOREIGN PATENT DOCUMENTS

EP 2574278 A2 4/2013
EP 2942028 A1 11/2015
(Continued)

OTHER PUBLICATIONS

U.S. Appl. No. 17/071,916 to Tschudy et. al., filed Oct. 15, 2020.
(Continued)

*Primary Examiner* — Adam Z Minchella
*Assistant Examiner* — Ashleigh Lauren Kern
(74) *Attorney, Agent, or Firm* — Carter, DeLuca & Farrell, LLP

(57) ABSTRACT

A robotic system includes an electrosurgical instrument having an instrument housing with a shaft and first and second jaw members attached thereto movable to grasp tissue. An input is coupled to a jaw drive rod and is configured to move the jaw members. A strain gauge is coupled to the jaw drive rod and is configured to measure an amount of strain thereon and communicate the amount of strain to a robotic controller. A handle is remotely disposed relative to the instrument housing and is configured to communicate with the input for controlling the jaw members. The handle includes a housing having components therein and a lever operably associated therewith such that movement of the lever relative to the housing correlates to movement of the jaw members. The components are configured to operably regulate the resistance of the lever in response to the amount of strain from the strain gauge.

15 Claims, 7 Drawing Sheets

(58) Field of Classification Search

CPC ..... A61B 34/70; A61B 17/2909; A61B 34/76; A61B 34/74; A61B 34/37; A61B 18/02; A61B 18/04; A61B 18/18; A61B 34/75; A61B 2018/00297; A61B 2018/00303; A61B 2018/00589; A61B 2018/00595; A61B 2018/00601; A61B 2018/00607; A61B 2018/0063; A61B 2090/061; A61B 2090/064

See application file for complete search history.

(56) References Cited

U.S. PATENT DOCUMENTS 5,848,986 A 12/1998 Lundquist et al.
6,817,974 B2 11/2004 Cooper et al.
7,799,028 B2 9/2010 Schechter et al.
7,861,906 B2 1/2011 Doll et al.
7,918,230 B2 4/2011 Whitman et al.
8,579,176 B2 11/2013 Smith et al.
9,055,961 B2 6/2015 Manzo et al.
9,474,569 B2 10/2016 Manzo et al.
10,731,740 B1 8/2020 Cui et al.
10,945,797 B2 3/2021 Anglese
11,058,504 B2 7/2021 Blanco et al.
2002/0099371 A1 7/2002 Schulze et al.
2002/0177842 A1 11/2002 Weiss
2003/0018331 A1* 1/2003 Dycus ................ A61B 18/1445 606/51
2003/0125734 A1 7/2003 Mollenauer
2003/0208186 A1 11/2003 Moreyra
2006/0022015 A1 2/2006 Shelton et al.
2006/0025811 A1 2/2006 Shelton
2006/0161138 A1 7/2006 Orban, III
2007/0233052 A1 10/2007 Brock
2008/0015631 A1 1/2008 Lee et al.
2008/0134812 A1 6/2008 Murata
2010/0274265 A1 10/2010 Wingardner et al.
2010/0292691 A1 11/2010 Brogna
2011/0118707 A1 5/2011 Burbank
2011/0118708 A1 5/2011 Burbank et al.
2011/0118709 A1 5/2011 Burbank
2011/0118754 A1 5/2011 Dachs, II et al.
2012/0116379 A1* 5/2012 Yates ................... A61B 17/295 606/33
2013/0123783 A1 5/2013 Marczyk et al.
2014/0276723 A1 9/2014 Parihar et al.
2015/0209061 A1* 7/2015 Johnson ................. A61B 90/03 606/171
2017/0042560 A1 2/2017 Lee et al.
2017/0150975 A1 6/2017 Bozung
2017/0265951 A1 9/2017 Grover et al.
2017/0273749 A1 9/2017 Grover et al.
2017/0365923 A1 12/2017 Schmutzler et al.
2018/0028271 A1 2/2018 Rockrohr
2018/0071037 A1 3/2018 Grover et al.
2018/0193096 A1* 7/2018 Nau, Jr .................. A61B 18/28
2019/0008600 A1 1/2019 Pedros et al.
2019/0015169 A1* 1/2019 Verner ................... A61B 34/76
2019/0099227 A1 4/2019 Rockrohr
2019/0274716 A1* 9/2019 Nott ..................... A61B 17/295
2019/0274769 A1 9/2019 Perdue et al.
2020/0022724 A1* 1/2020 Worrell ............. A61B 18/1442
2020/0237453 A1 7/2020 Anglese
2020/0237455 A1 7/2020 Anglese
2020/0246011 A1 8/2020 Sgroi, Jr. et al.
2020/0246058 A1 8/2020 Traina
2020/0253676 A1 8/2020 Traina
2020/0261166 A1 8/2020 Anglese
2020/0261167 A1 8/2020 Anglese
2020/0261168 A1 8/2020 Anglese
2020/0367984 A1 11/2020 Peine et al.

FOREIGN PATENT DOCUMENTS

EP 3508145 A1 7/2019
JP 2015525609 A 9/2015
JP 2021509042 A 3/2021
WO 2012061638 A1 5/2012
WO 2014004114 A1 1/2014

OTHER PUBLICATIONS

U.S. Appl. No. 63/183,089 to Tschudy et al., filed May 3, 2021.
Extended European Search Report 22190433.7 dated May 25, 2023, 10pp.
Japanese Office Action issued in corresponding Japanese Application No. 2022-129284 mailed Apr. 2, 2026, 7 pages.
Communication Pursuant to Article 94(3) EPC issued in corresponding European Application No. 22 190 433.7 dated Jun. 12, 2026, 8 pages.

* cited by examiner 120
110
484
484
130
600
480
452
480
456
450
400
600e
454
600d
440
420
600d
430
600c
484

END EFFECTOR DRIVE MECHANISMS FOR SURGICAL INSTRUMENTS SUCH AS FOR USE IN ROBOTIC SURGICAL SYSTEMS

FIELD

The present disclosure relates to surgical instruments and, more specifically, to end effector drive mechanisms for surgical instruments such as for use in robotic surgical systems.

BACKGROUND

Robotic surgical systems are increasingly utilized in various different surgical procedures. Some robotic surgical systems include a console supporting a robotic arm. One or more different surgical instruments may be configured for use with the robotic surgical system and selectively mountable to the robotic arm. The robotic arm provides one or more inputs to the mounted surgical instrument to enable operation of the mounted surgical instrument.

A surgical forceps, one type of instrument capable of being utilized with a robotic surgical system, relies on mechanical action between its jaw members to grasp, clamp, and constrict tissue. Electrosurgical forceps utilize both mechanical clamping action and energy to heat tissue to treat, e.g., coagulate, cauterize, or seal, tissue. Typically, once tissue is treated, the tissue is severed using a cutting element. Accordingly, electrosurgical forceps are designed to incorporate a cutting element to effectively sever treated tissue. Alternatively, energy-based, e.g., thermal, electrical, ultrasonic, etc., cutting mechanisms may be implemented.

With traditional surgical instrumentation, e.g., open and endoscopic surgical instrumentation, the surgeon is typically able to feel or otherwise sense direct feedback from the end effector relating to the size of the tissue between the jaw members as well as the force being applied during manipulation and sealing. With robotic instrumentation, haptic feedback may be lost or sacrificed for ease of use to offset among other things, surgical fatigue.

SUMMARY

As used herein, the term “distal” refers to the portion that is being described which is farther from an operator (whether a human surgeon or a surgical robot), while the term “proximal” refers to the portion that is being described which is closer to the operator. The terms “about,” substantially,” and the like, as utilized herein, are meant to account for manufacturing, material, environmental, use, and/or measurement tolerances and variations, and in any event may encompass differences of up to 10%. Further, to the extent consistent, any of the aspects described herein may be used in conjunction with any or all of the other aspects described herein.

Provided in accordance with aspects of the present disclosure is a robotic surgical system including an electrosurgical instrument including an instrument housing having a shaft extending therefrom. An end effector assembly is disposed at a distal end of the shaft and includes first and second jaw members movable between a first position wherein at least one of the jaw members is spaced relative to the other of the jaw members and a second position wherein the first and second jaw members cooperate to grasp tissue. An input is operably disposed within the instrument housing and is operably coupled to a jaw drive rod configured to move the jaw members between the first and second positions upon actuation thereof. A strain gauge is operably coupled to the jaw drive rod and is configured to measure an amount of strain thereon and communicate the amount of strain to a robotic controller operably coupled to the input.

One or more handles is remotely disposed relative to the instrument housing and is configured to communicate with the input for controlling the movement of the jaw members. The handle includes a housing having a lever operably coupled thereto, the housing including a cavity defined therein configured to house one or more components therein configured to operably connect to the input such that movement of the lever relative to the housing correlates to movement of the jaw members between the first and second positions. The one or more components are configured to operably regulate the resistance of the lever in response to the amount of strain from the strain gauge.

In aspects according to the present disclosure, the one or more components are configured to operably regulate the resistance of the lever relative to a baseline strain measurement measured during manufacturing. In other aspects according to the present disclosure, the one or more components are configured to operably regulate the resistance of the lever relative to a strain curve.

In aspects according to the present disclosure, the correlation of the resistance of the lever to the strain on the jaw drive rod is linear. In other aspects according to the present disclosure, the correlation of the resistance of the lever to the strain on the jaw drive rod is non-linear.

In aspects according to the present disclosure, the combination of components disposed in the cavity include levers, gears, linkages, and springs.

Provided in accordance with aspects of the present disclosure is a robotic surgical system including an electrosurgical instrument including an instrument housing having a shaft extending therefrom. An end effector assembly is disposed at a distal end of the shaft and includes first and second jaw members movable between a first position wherein at least one of the jaw members is spaced relative to the other of the jaw members and a second position wherein the first and second jaw members cooperate to grasp tissue. An input is operably disposed within the instrument housing and is operably coupled to a jaw drive rod configured to move the jaw members between the first and second positions upon actuation thereof. A spring is operably coupled to the jaw drive rod and configured to regulate the closure pressure between the jaw members. A strain gauge is operably coupled to the jaw drive rod, spring, first jaw member and/or second jaw member. The strain gauge is configured to measure an amount of strain on the jaw drive rod, spring, first jaw member and/or second jaw member and communicate the amount of strain to a robotic controller operably coupled to the input.

One or more handles is remotely disposed relative to the instrument housing and is configured to communicate with the input for controlling the movement of the jaw members. The handle includes a housing having a lever operably coupled thereto, the housing including a cavity defined therein configured to house one or more components therein configured to operably connect to the input such that movement of the lever relative to the housing correlates to movement of the jaw members between the first and second positions. The one or more components are configured to operably regulate the resistance of the lever in response to the amount of strain from the strain gauge.

In aspects according to the present disclosure, the one or more components are configured to operably regulate the resistance of the lever relative to a baseline strain measurement measured during manufacturing. In other aspects according to the present disclosure, the one or more components are configured to operably regulate the resistance of the lever relative to a strain curve.

In aspects according to the present disclosure, the correlation of the resistance of the lever to the strain on the jaw drive rod is linear. In other aspects according to the present disclosure, the correlation of the resistance of the lever to the strain on the jaw drive rod is non-linear.

In aspects according to the present disclosure, the combination of components disposed in the cavity include levers, gears, linkages, and springs.

Provided in accordance with aspects of the present disclosure is a robotic surgical system including an electrosurgical instrument including an instrument housing having a shaft extending therefrom. An end effector assembly is disposed at a distal end of the shaft and includes first and second jaw members movable between a first position wherein at least one of the jaw members is spaced relative to the other of the jaw members and a second position wherein the first and second jaw members cooperate to grasp tissue. An input is operably disposed within the instrument housing and operably coupled to a jaw drive rod, the jaw drive rod cooperating with a spring to move the jaw members between the first and second positions under a closure pressure upon actuation thereof. A proximity device is operably coupled to one or both jaw members or the spring and is configured to detect an aperture between the jaw members and communicate a size of the aperture to a robotic controller operably coupled to the input.

One or more handles is remotely disposed relative to the instrument housing and is configured to communicate with the input for controlling the movement of the jaw members. The handle includes a housing having a lever operably coupled thereto, the housing including a cavity defined therein configured to house one or more components therein configured to operably connect to the input such that movement of the lever relative to the housing correlates to movement of the jaw members between the first and second positions. The one or more components are configured to operably regulate the resistance of the lever in response to the size of the aperture detected by the proximity sensor.

In aspects according to the present disclosure, the proximity device includes at least one of a proximity sensor, camera or potentiometer.

In aspects according to the present disclosure, the proximity device is operably coupled to the spring and measures the size of the aperture based upon the movement of the spring. In other aspects according to the present disclosure, the proximity device is operably coupled to one or both of the jaw members and measures the size of the aperture based upon the movement of the jaw member(s).

BRIEF DESCRIPTION OF THE DRAWINGS

Various aspects and features of the present disclosure are described hereinbelow with reference to the drawings wherein.

DETAILED DESCRIPTION

Figure 1:
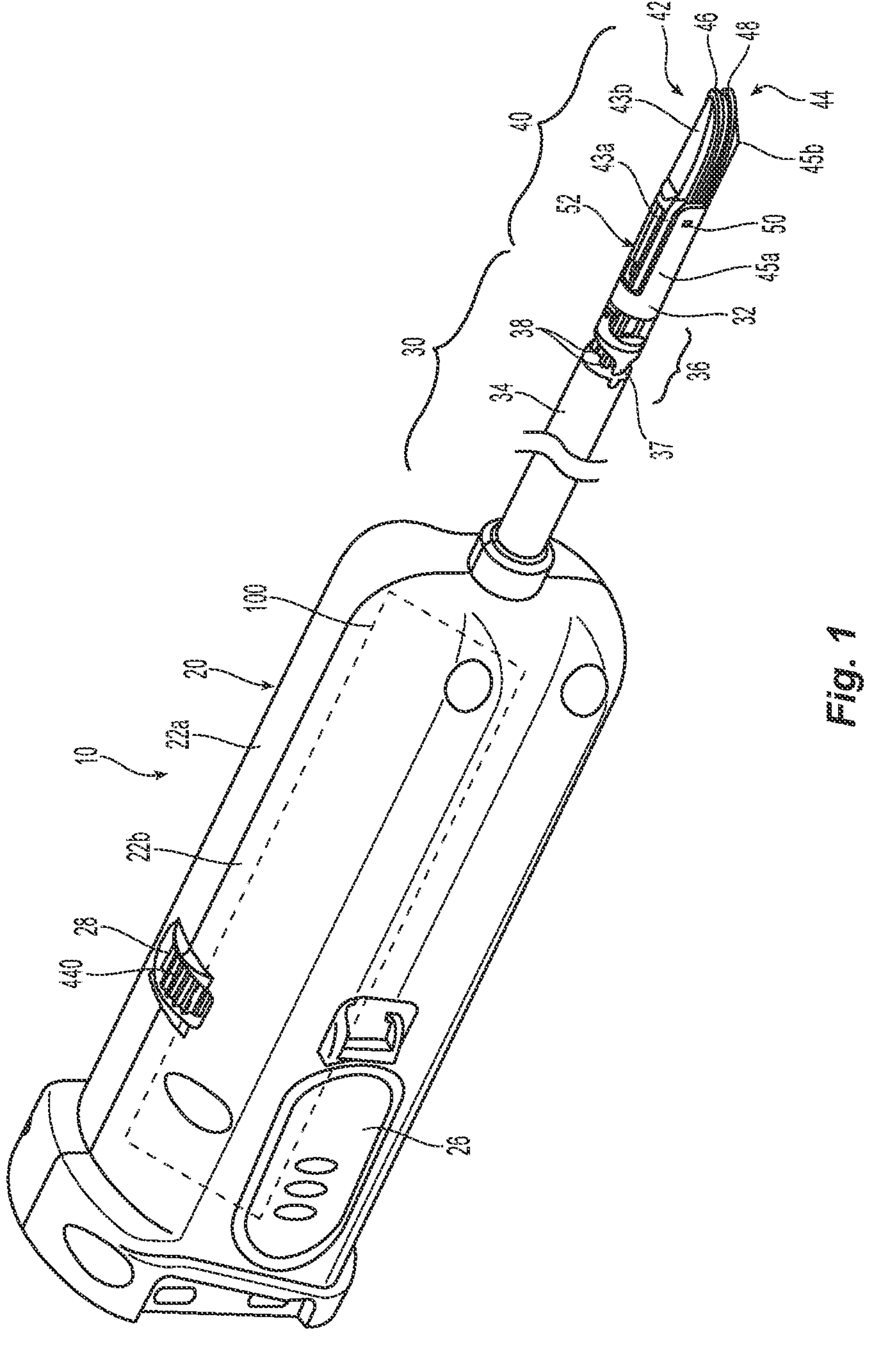
FIG. 1 is a perspective view of a surgical instrument in accordance with the present disclosure configured for mounting on a robotic arm of a robotic surgical system.
Figure 2:
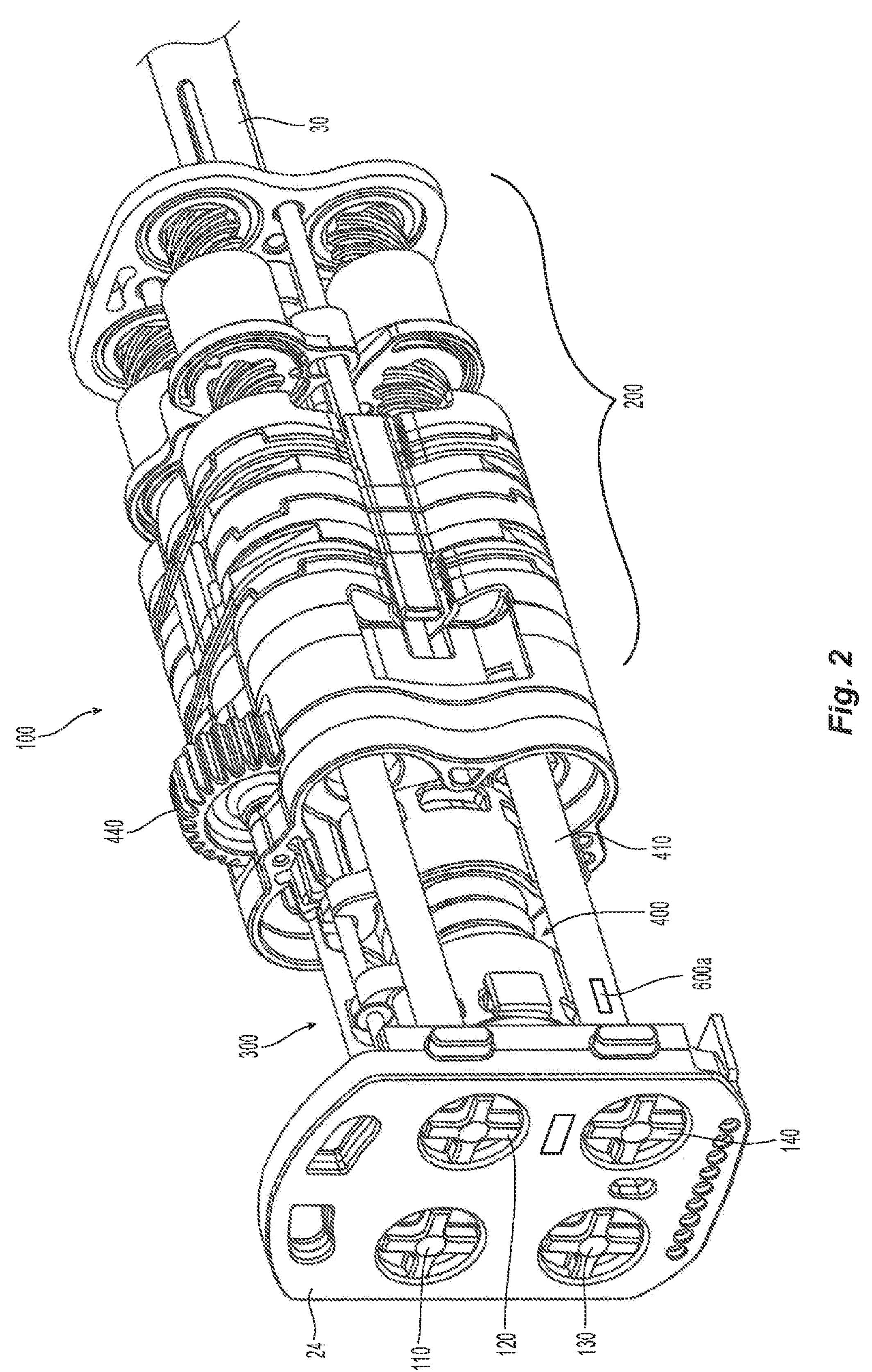
FIG. 2 is a rear perspective view of a proximal portion of the surgical instrument of FIG. 1 with an outer housing removed.
Figure 3:
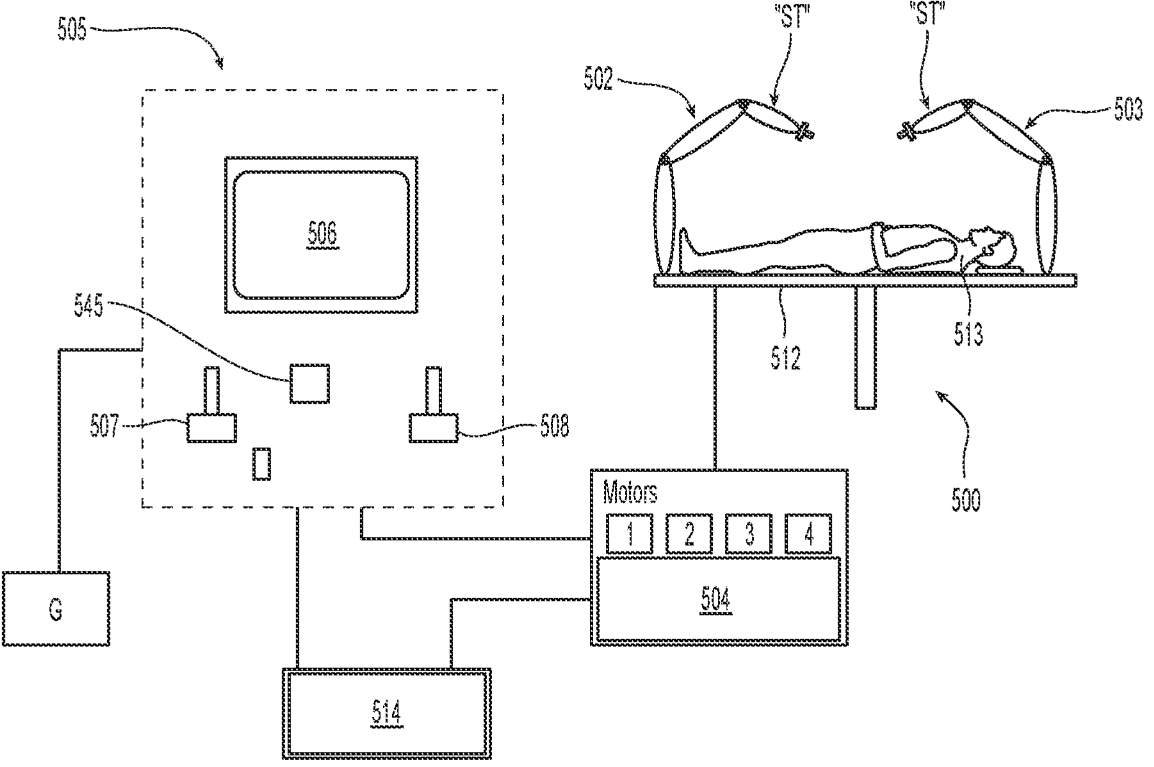
FIG. 3 is a schematic illustration of an exemplary robotic surgical system configured to releasably receive the surgical instrument of FIG. 1.

Referring to FIGS. 1 and 2, a surgical instrument 10 provided in accordance with the present disclosure generally includes a housing 20, a shaft 30 extending distally from housing 20, an end effector assembly 40 extending distally from shaft 30, and an actuation assembly 100 disposed within housing 20 and operably associated with shaft 30 and end effector assembly 40. Instrument 10 is detailed herein as an articulating electrosurgical forceps configured for use with a robotic surgical system, e.g., robotic surgical system 500 (FIG. 3). However, the aspects and features of instrument 10 provided in accordance with the present disclosure, detailed below, are equally applicable for use with other suitable surgical instruments (including non-robotic surgical instrument) and/or in other suitable surgical systems (including non-robotic surgical systems).

Housing 20 of instrument 10 includes first and second body portion 22*a*, 22*b* and a proximal face plate 24 (FIG. 2) that cooperate to enclose actuation assembly 100 therein. Proximal face plate 24 includes apertures defined therein through which inputs 110-140 of actuation assembly 100 extend. A pair of latch levers 26 (only one of which is illustrated in FIG. 1) extend outwardly from opposing sides of housing 20 and enables releasable engagement (directly or indirectly) of housing 20 with a robotic arm of a surgical system, e.g., robotic surgical system 500 (FIG. 3). An aperture 28 defined through housing 20 permits thumbwheel 440 to extend therethrough to enable manual manipulation of thumbwheel 440 from the exterior of housing 20 to permit manual opening and closing of end effector assembly 40.

Shaft 30 of instrument 10 includes a distal segment 32, a proximal segment 34, and an articulating section 36 disposed between the distal and proximal segments 32, 34, respectively. Articulating section 36 includes one or more articulating components 37, e.g., links, joints, etc. A plurality of articulation cables 38, e.g., four (4) articulation cables, or other suitable actuators, extends through articulating section 36. More specifically, articulation cables 38 are operably coupled to distal segment 32 of shaft 30 at the distal ends thereof and extend proximally from distal segment 32 of shaft 30, through articulating section 36 of shaft 30 and proximal segment 34 of shaft 30, and into housing 20, wherein articulation cables 38 operably couple with an articulation assembly 200 of actuation assembly 100 to enable selective articulation of distal segment 32 (and, thus end effector assembly 40) relative to proximal segment 34 and housing 20, e.g., about at least two axes of articulation (yaw and pitch articulation, for example). Articulation cables 38 are arranged in a generally rectangular configuration, although other suitable configurations are also contemplated.

With respect to articulation of end effector assembly 40 relative to proximal segment 34 of shaft 30, actuation of articulation cables 38 is effected in pairs. More specifically, in order to pitch end effector assembly 40, the upper pair of cables 38 is actuated in a similar manner while the lower pair of cables 38 is actuated in a similar manner relative to one another but an opposite manner relative to the upper pair of cables 38. With respect to yaw articulation, the right pair of cables 38 is actuated in a similar manner while the left pair of cables 38 is actuated in a similar manner relative to one another but an opposite manner relative to the right pair of cables 38.

Distal segment 32 of shaft 30 defines a clevis portion of end effector assembly 40 that supports first and second jaw members 42, 44, respectively. Each jaw member 42, 44 includes a proximal extension portion 43*a*, 45*a* and a distal body portion 43*b*, 45*b*, respectively. Distal body portions 43*b*, 45*b* define opposed tissue-contacting surfaces 46, 48, respectively. Proximal extension portions 43*a*, 45*a* are pivotably coupled to one another about a pivot pin 50 and are operably coupled to one another via a cam drive mechanism 52 (described in greater detail below) to enable pivoting of jaw member 42 relative to jaw member 44 and distal segment 32 of shaft 30 between a spaced-apart position (e.g., an open position of end effector assembly 40) and an approximated position (e.g., a closed position of end effector assembly 40) for grasping tissue between tissue-contacting surfaces 46, 48. As an alternative to this unilateral configuration, a bilateral configuration may be provided whereby both jaw members 42, 44 are pivotable relative to one another and distal segment 32 of shaft 30.

Opposing longitudinally-extending channels (not shown) are defined through tissue-contacting surfaces 46, 48, respectively, of jaw members 42, 44. A translating cutting element (not shown) is provided and selectively advanceable to enable cutting of tissue grasped between tissue-contacting surfaces 46, 48 of jaw members 42, 44, respectively. A cutting drive assembly 300 (FIG. 2) of actuation assembly 100 provides for selective actuation of cutting element through channel(s) of jaw members 42, 44 to cut tissue grasped between tissue-contacting surfaces 46, 48. Cutting drive assembly 300 is operably coupled to third input 130 of actuation assembly 100 such that, upon receipt of appropriate rotational input into third input 130, cutting drive assembly 300 advances the cutting element between jaw members 42, 44 to cut tissue grasped between tissue-contacting surfaces 46, 48.

Continuing with reference to FIGS. 1 and 2, a drive rod (not shown) is operably coupled to end effector assembly 40 such that longitudinal actuation of drive rod pivots jaw member 42 relative to jaw member 44 between the spaced-apart and approximated positions, as detailed below. More specifically, urging drive rod proximally pivots jaw member 42 relative to jaw member 44 towards the approximated position while urging drive rod distally pivots jaw member 42 relative to jaw member 44 towards the spaced-apart position. However, the reverse configuration is also contemplated. Drive rod extends proximally from end effector assembly 40 through shaft 30 and into housing 20 wherein drive rod is operably coupled with a jaw drive assembly 400 of actuation assembly 100 to enable selective actuation of end effector assembly 40 to grasp tissue therebetween and apply a closure force within an appropriate jaw closure force range, e.g., in response to an appropriate rotational input into fourth input 140.

Tissue-contacting surfaces 46, 48 of jaw members 42, 44, respectively, are at least partially formed from an electrically conductive material and are energizable to different potentials to enable the conduction of electrical energy through tissue grasped therebetween, although tissue-contacting surfaces 46, 48 may alternatively be configured to supply any suitable energy, e.g., thermal, microwave, light, ultrasonic, etc., through tissue grasped therebetween for energy-based tissue treatment. Instrument 10 defines conductive pathways extending through housing 20 and shaft 30 to end effector assembly 40 that may include lead wires, contacts, and/or electrically-conductive components to enable electrical connection of tissue-contacting surfaces 46, 48 of jaw members 42, 44, respectively, to an energy source (not shown), e.g., an electrosurgical generator via an electrosurgical cable extending therebetween, for supplying energy to tissue-contacting surfaces 46, 48 to treat, e.g., seal, tissue grasped between tissue-contacting surfaces 46, 48.

Actuation assembly 100 is disposed within housing 20 and includes articulation assembly 200, cutting drive assembly 300, and jaw drive assembly 400. Articulation assembly 200 is operably coupled between first and second inputs 110, 120, respectively, of actuation assembly 100 and articulation cables 38 such that, upon receipt of appropriate rotational inputs into first and/or second inputs 110, 120, articulation assembly 200 manipulates cables 38 (FIG. 1) to articulate end effector assembly 40 in a desired direction, e.g., to pitch and/or yaw end effector assembly 40. Cutting drive assembly 300, as noted above, enables reciprocation of the cutting element between jaw members 42, 44 to cut tissue grasped between tissue-contacting surfaces 46, 48 in response to receipt of appropriate rotational input into third input 130. Jaw drive assembly 400 is operably coupled between fourth input 140 of actuation assembly 100 and drive rod such that, upon receipt of appropriate rotational input into fourth input 140, jaw drive assembly 400 pivots jaw members 42, 44 between the spaced-apart and approximated positions to grasp tissue therebetween and apply a closure force within an appropriate closure force range.

Actuation assembly 100 is configured to operably interface with a robotic surgical system 500 (FIG. 3) when instrument 10 is mounted on robotic surgical system 500 (FIG. 3), to enable robotic operation of actuation assembly 100 to provide the above-detailed functionality. That is, robotic surgical system 500 (FIG. 3) selectively provides rotational inputs to inputs 110-140 of actuation assembly 100 to articulate end effector assembly 40, grasp tissue between jaw members 42, 44, and/or cut tissue grasped between jaw members 42, 44. However, it is also contemplated that actuation assembly 100 be configured to interface with any other suitable surgical system, e.g., a manual surgical handle, a powered surgical handle, etc. For the purposes herein, robotic surgical system 500 (FIG. 3) is generally described.

Turning to FIG. 3, a schematic representation of a robotic surgical system 500 is configured for use in accordance with the present disclosure. Aspects and features of robotic surgical system 500 not germane to the understanding of the present disclosure are omitted to avoid obscuring the aspects and features of the present disclosure in unnecessary detail.

Robotic surgical system 500 generally includes a plurality of robot arms 502, 503; a control device 504; and an operating console 505 coupled with control device 504. Operating console 505 may include a display device 506, which may be set up in particular to display three-dimensional images; and manual input devices or handles 507, 508, by means of which a person, e.g., a surgeon, may be able to telemanipulate robot arms 502, 503 in a first operating mode. Robotic surgical system 500 may be configured for use on a patient 513 lying on a patient table 512 to be treated in a minimally invasive manner. Robotic surgical system 500 may further include a database 514, in particular coupled to control device 504, in which are stored, for example, pre-operative data from patient 513 and/or anatomical atlases.

Each of the robot arms 502, 503 may include a plurality of members, which are connected through joints, and a mounted device which may be, for example, a surgical tool "ST." One or more of the surgical tools "ST" may be instrument 10 (FIG. 1), thus providing such functionality on a robotic surgical system 500.

Robot arms 502, 503 may be driven by electric drives, e.g., motors, connected to control device 504. Control device 504, e.g., a computer, may be configured to activate the motors, in particular by means of a computer program, in such a way that robot arms 502, 503, and, thus, their mounted surgical tools "ST" execute a desired movement and/or function according to a corresponding input from manual input devices 507, 508, respectively. Control device 504 may also be configured in such a way that it regulates the movement of robot arms 502, 503 and/or of the motors.

Figure 4A:
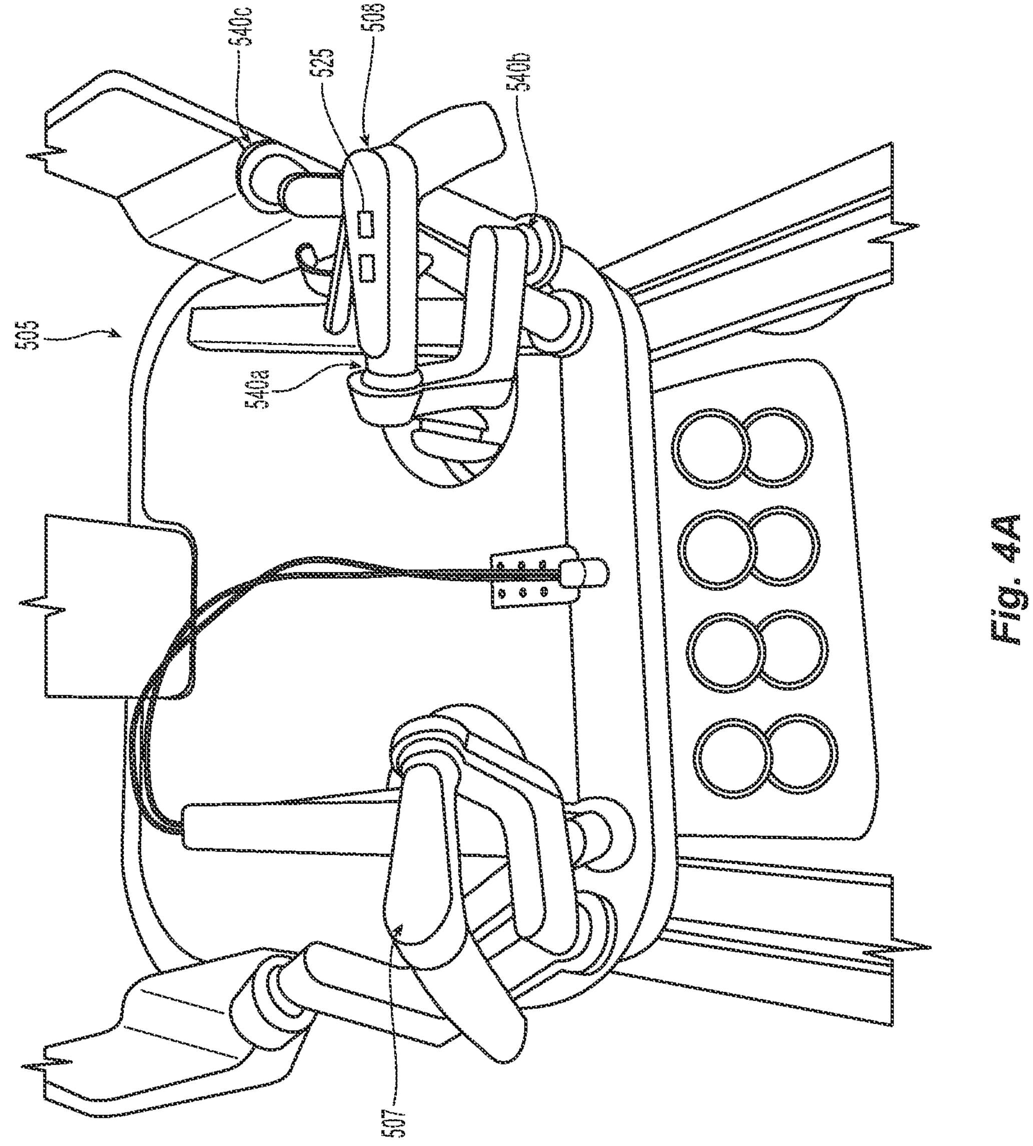
FIG. 4A is a top perspective view of the robotic surgical system of FIG. 3 showing a pair of operating handles for remotely controlling the surgical instrument.
Figure 4B:
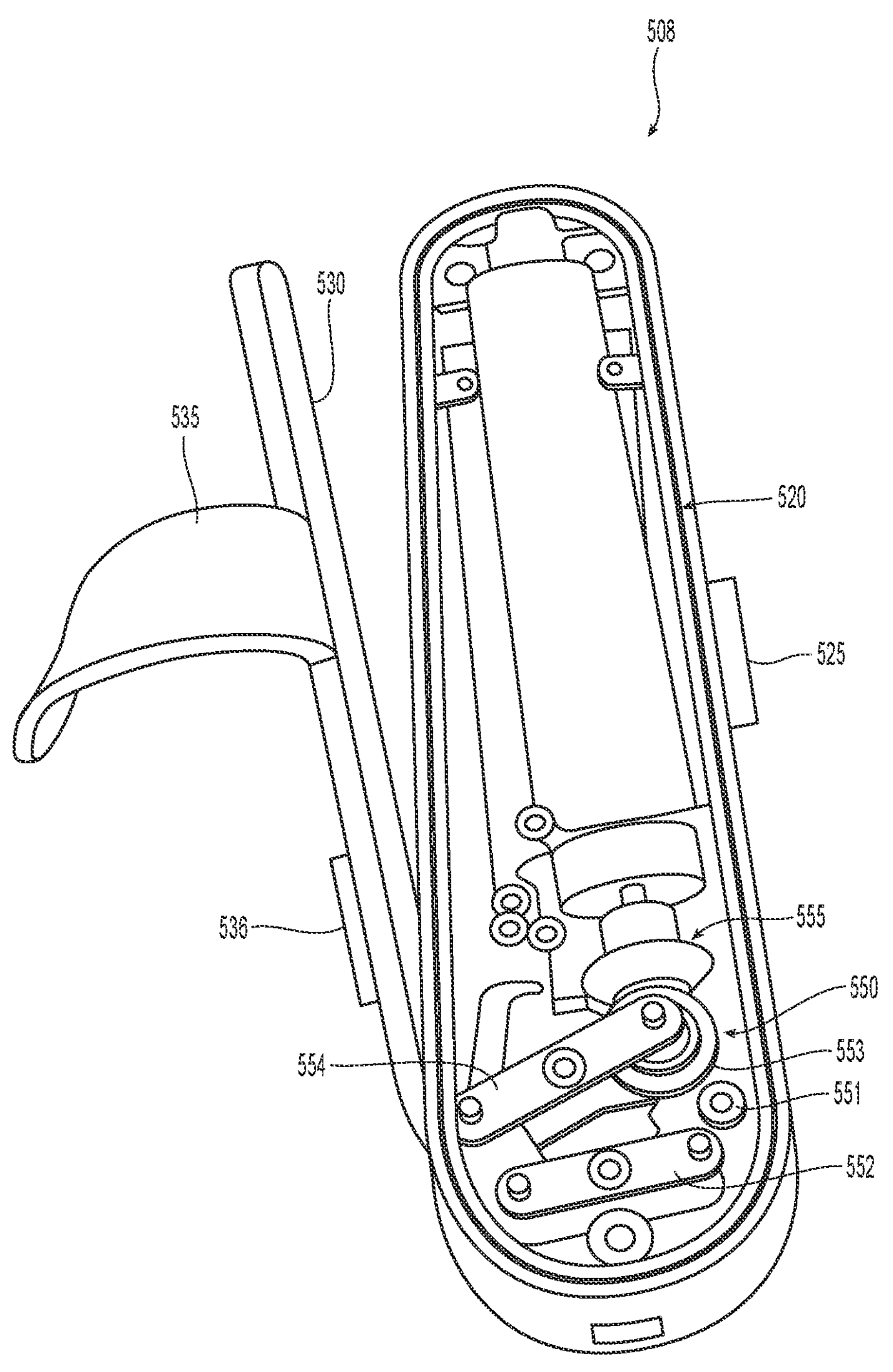
FIG. 4B is an enlarged view of one of the operating handles of the robotic surgical system of FIG. 4A.

Turning now to FIGS. 4A and 4B, portions of the operating console 505 are depicted in more detail, namely, input devices or handles 507, 508. Each input device or handle 507, 508 includes similar components and, as such, only input device or handle 508 is depicted in FIG. 4B. Input device 508 includes a housing 520 defining a cavity 521 therein configured to house an actuation assembly 550 configured to communicate with one or more of the inputs 110-140 described in detail above. Housing 520 may be coupled to one or more gimbal mechanisms 540*a*-540*c* to control the extension, rotation, articulation, et. al. of the end effector assembly 40 as described above. Details relating to the various types of gimbal mechanisms that may be utilized for this purpose are disclosure in U.S. patent application Ser. No. 16/306,420, filed Nov. 30, 2018 entitled CONTROL ARM ASSEMBLIES FOR ROBOTIC SURGICAL SYSTEMS, the entire contents of which are incorporated by reference herein.

Actuation assembly 550 is operatively coupled to a lever 530 which, upon actuation thereof relative to housing 520, opens and closes jaw members 42, 44 of end effector assembly 40. More particularly, lever 530 couples to a series of components, e.g., links, couplers, and/or actuators 551-555, configured for communication with input 140 for controlling the closure of jaw members 42, 44 relative to one another as described above. Although depicted as a series of links, couplers and/or actuators 551-555, any type of mechanical or electromechanical arrangement is contemplated. Moreover, and as explained below, actuation of lever 530 relative to the actuation of the jaw members 42, 44 may be linear 1:1, non-linear 1:2 or variable during the entire range of movement or stroke of the lever 530.

Lever 530 includes a finger support 535 which is configured to facilitate relative movement of the lever 530 to the housing 520. More particularly, finger support 535 may be cuff-like to envelop one or more fingers of the user to promote retraction of the lever 530 away from the housing 520 and facilitate rotation of the housing about one or more of the above-identified gimbal mechanisms 540*a*-540*c*.

As mentioned above, during robotic surgery involving the sealing of vessels or tissue, it is important that the surgeon adequately control the pressure between the jaw members 42, 44 both when grasping and manipulating tissue and when clamping on a vessel or tissue to create a seal. As can be appreciated, the pressure between jaw members 42, 44 when delicately grasping and manipulating vessels or tissue is significantly less than when sealing vessels or tissue. The haptic feedback or "feel" of the jaw members 42, 44 is not always appropriately conveyed back the surgeon through the handles 508.

The various above-mentioned actuation assemblies, levers, gears, linkages, and springs discussed above all work in concert to facilitate actuation of the jaw members 42, 44 from the remote input devices or handles 507, 508. Typically, movement of the lever 530 a fixed distance relative to housing 520 will actuate the jaw members 42, 44 under the same force irrespective of the size of the vessel or tissue.

For example, with robotic vessel sealing devices such as those described above, the actuation of the jaw members 42, 44 is controlled through motor rotations which are mapped to the actuation lever 530. Since the forces required to generate a proper seal are typically on the order of 100 psi or greater, the software maps the relative movement of the surgeon's fingers and lever 530 to the housing 520 and correlates this relative movement to the jaw members 42, 44. Various software algorithms are utilized for this purpose. As a result, very little force is required to move the lever 530 relative to the housing 520 via the surgeon's fingers to generate the proper pressure for sealing tissue. This also helps to offset surgical fatigue. However, since the robotic sealer is designed to generate sealing pressures at the jaw members 42, 44 with far less comparative forces at the lever 530, in some instances too much pressure, e.g., pressures associated with sealing tissue, may be applied to a vessel or tissue bundle when the surgeon's intention is to simply grasp, manipulate or cut tissue.

Figure 5:
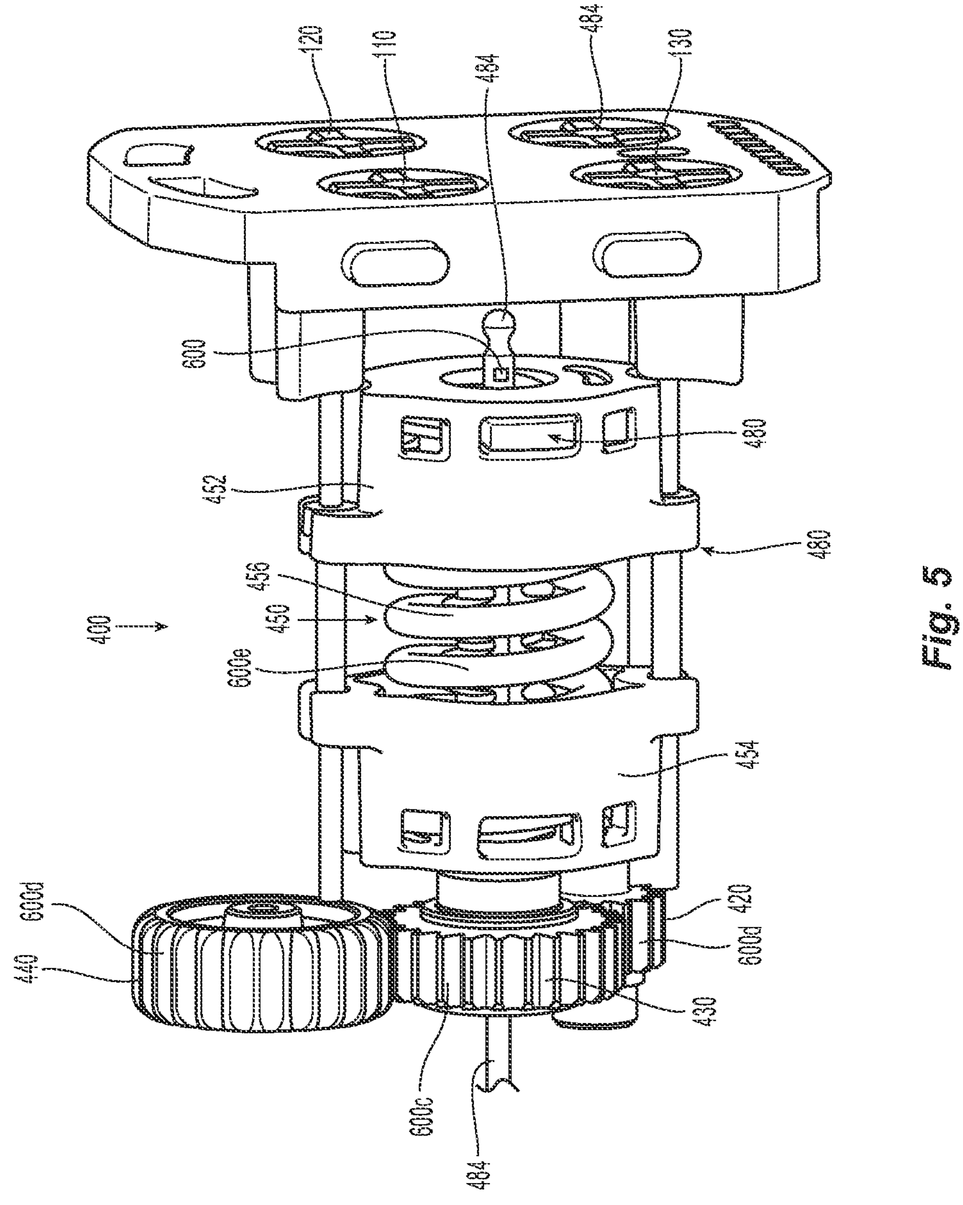
FIG. 5 is an enlarged internal view of the surgical instrument showing a strain gauge disposed therein.
Figure 6:
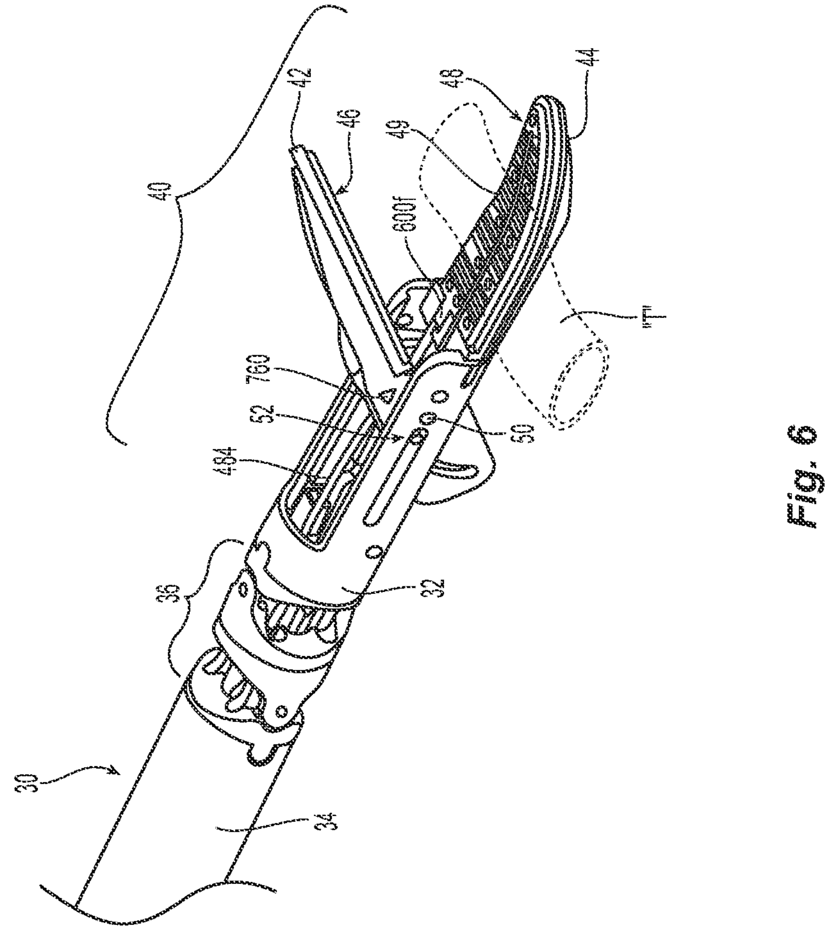
FIG. 6 is an enlarged view of an end effector assembly of the surgical instrument.

FIGS. 5 and 6 show views of the housing 20 of the instrument 10 with an internal view of a drive rod 484 which is configured to operably couple to cam-slot assembly 52 of end effector assembly 40, e.g., engaged with the cam pin thereof, such that longitudinal actuation of drive rod 484 pivots jaw member 42 relative to jaw member 44 between the spaced-apart and approximated positions. More specifically, urging drive rod 484 proximally pivots jaw member 42 relative to jaw member 44 towards the approximated position while urging drive rod 484 distally pivots jaw member 42 relative to jaw member 44 towards the spaced-apart position. However, other suitable mechanisms and/or configurations for pivoting jaw member 42 relative to jaw member 44 between the spaced-apart and approximated positions in response to selective actuation of drive rod 484 are also contemplated. Drive rod 484 extends proximally from end effector assembly 40 through shaft 30 and into housing 20 wherein drive rod 484 is operably coupled with the jaw drive assembly 400 of actuation assembly 100 (FIGS. 2 and 5) to enable selective actuation of end effector assembly 40 to grasp tissue therebetween and apply a closure pressure within a closure pressure range of about 3 $kg/cm^2$ to about 16 kg/cm', as detailed below.

Tissue-contacting surfaces 46, 48 of jaw members 42, 44, respectively, are at least partially formed from an electrically conductive material and are energizable to different potentials to enable the conduction of RF electrical energy through tissue grasped therebetween, although tissue-contacting surfaces 46, 48 may alternatively be configured to supply any suitable energy, e.g., thermal, microwave, light, ultrasonic, ultrasound, etc., through tissue grasped therebetween for energy-based tissue treatment.

In one embodiment, in order to convey haptic feedback to the handle 508 of the instrument 10, a strain gauge 600 is operably coupled to the jaw drive rod 484 to measure the strain associated therewith during actuation. With larger tissue types, additional strain is placed on the jaw drive rod 484 which is measured by the strain gauge 600. The strain gauge 600, in turn, conveys the measurement feedback to the robotic controller 505 or control device 504 and the handle 508 to adjust (e.g., increase or decrease) the resistance of the lever 530 to provide haptic feedback to the surgeon.

Any changes in strain measured by the strain gauge 600 are converted into haptic feedback, e.g., resistance, in the lever 530. As can be appreciated and depending upon the sensitivity of the correlation of the strain gauge 600 and the lever 530, the surgeon would be able to remotely "feel" differences in tissue, e.g., thickness, amount, etc., disposed between the jaw members 42, 44 and the relative closure pressure being applied thereto.

As mentioned above, actuation assembly 550 (and components 551-555) is operatively coupled to a lever 530 which, upon actuation, opens and closes jaw members 42, 44 of end effector assembly 40. The components 551-555 operably couple or are configured for communication with input 140 for controlling the closure of jaw members 42, 44 relative to one another as described above. Depending upon the actual feedback from strain gauge 600, actuation of lever 530 relative to the actuation of the jaw members 42, 44 may be linear 1:1, non-linear 1:2 or variable during the entire range of movement or stroke of the lever 530. As can be appreciated, a variable correlation between the lever 530 and the jaw members 42, 44 may lessen the overall lever force required to generate the appropriate closure pressure at the jaw members 42, 44 for certain instrument functions, e.g., sealing tissue. For simple manipulation, grasping and cutting, the ratio of the lever force to jaw closure pressure may be linear 1:1 or even have a reverse ratio 2:1 depending upon a particular purpose. For sealing tissue, the ratios may be greater.

In embodiments, the strain gauge 600 may need to be calibrated during manufacturing or during a so-called "homing" operation as new end effector assemblies 40 are interchanged. Details relating to various homing algorithms are disclosed in commonly-owned U.S. Patent Application Ser. No. 63/183,089 entitled MOTOR POSITION CONTROL AND METHODS FOR ROBOTIC ASSISTED SEALING INSTRUMENT, the entire contents of which being incorporated by reference herein. As mentioned in therein, during manufacturing or a homing step, a baseline measurement of the strain on the strain gauge 600 may be recorded (or recorded against a baseline strain curve) and the robotic controller 505 or control device 504 which is utilized by a software algorithm (or drive assembly 550 or one or more individual components 551-555) adjusts the lever 530 accordingly. As the strain gauge 600 continually measures strain, the force required to actuate the lever 530 is adjusted accordingly, e.g., along a strain curve, depending upon the intended function of the instrument, e.g., grasp or seal.

A switch 536 may be operably coupled to handle 508 and utilized to convey the surgeon's intent to the software for allocating the correct haptic response. Alternatively, one or more activation switches 525 may be included on the handle 508 which supply electrosurgical energy to the jaw members 42, 44 for sealing tissue. Activation of one or more of the switches 525 may adjust the strain curve to correlate the resistive force of the lever 530 with a sealing pressure between the jaw members 42, 44. A delay may be instituted in the software algorithm to accomplish this purpose.

Any type mechanical, optical, acoustical, pneumatic or electrical strain gauge 600 may be employed for this purpose. Moreover, the strain gauge 600 may be operably coupled to one or more of the internal components of the instrument 10 that move in response to actuation of the lever 530. For example and with reference to FIGS. 2 and 5, jaw drive assembly 400 of actuation assembly 100 is shown generally including an input shaft 410, an input gear 420, a drive gear 430, a thumbwheel 440, a spring force assembly 450, and a drive rod assembly 480. Thumbwheel 440 is also disposed in meshed engagement with drive gear 430 such that rotation of thumbwheel 440 effects rotation of drive gear 430 in an opposite direction, thus enabling manual driving of drive gear 430 via manipulation of thumbwheel 440. Spring force assembly 450 includes a proximal hub 452, a distal hub 454, and a compression spring 456. Further details relating to the internal working components of the instrument 10 are disclosed in commonly-owned U.S. patent application Ser. No. 17/071,916 filed Oct. 15, 2020 the entire contents of which being incorporated by reference herein.

For example, the strain gauge 600 may be operably coupled to input shaft 410 (strain gauge 600*a*), the input gear 420 (strain gauge 600*b*), the drive gear 430 (strain gauge 600*c*), the thumbwheel 440 (strain gauge 600*d*), the spring force assembly 450 or spring 456 (strain gauge 600*e*), and/or the drive rod assembly 480. Moreover, it is contemplated to include multiple strain gauges 600*a*-600*e* on one or more of these various components to more accurately supply haptic feedback to the surgeon during use.

As mentioned above, the jaw members 42, 44 include respective opposed tissue-contacting surfaces 46, 48 configured to receive electrosurgical energy of opposite potentials from an electrosurgical energy source, e.g., a generator "G" such that, when the generator "G" is activated, tissue disposed between the opposing tissue-contacting surfaces 46, 48 is treated. One or more strain gauges 600*f* may be operably associated with one or more components of the jaw members, e.g., tissue-contacting surfaces 46, 48, or any other part of the jaw members 42, 44.

Once measured, the strain gauge (strain gauges 600*a*-600*f* collectively referred hereinafter as strain gauges 600) communicates to the robotic controller 505 or control device 504 to provide feedback to the handle 508 to adjust the haptic feedback or resistance of the lever 535 according to the strain measurement. As mentioned above, the surgeon would be able to remotely "feel" differences in tissue, e.g., thickness, amount, etc., disposed between the jaw members 42, 44 and the relative closure pressure being applied thereto. For simple manipulation, grasping and cutting, the ratio of the lever force to jaw closure pressure may be linear 1:1 or even have a reverse ratio 2:1 depending upon a particular purpose. For sealing tissue, the ratios may be greater. Moreover, and as explained above, actuation of lever 530 relative to the actuation of the jaw members 42, 44 may be non-linear 1:2 or variable during the entire range of movement or stroke of the lever 530.

Various visual or audible feedback 545 may be conveyed to the surgeon relating to the amount of tissue between the jaw members 42, 44 and the requisite pressure to be applied for the intended tissue action, e.g., manipulation, grasping, cutting or sealing. The feedback may be as simple as a "SAFE" signal when the surgeon intends to manipulate, grasp or cut tissue, e.g., green light, safe tone, or may be metered in relation to the amount of pressure being applied to tissue. Metering of the feedback either visually or audibly may provide feedback to the surgeon when he/she is approaching unintended pressures between the jaw members 42, 44 for these tissue actions.

Switch 536 may be utilized to convey the surgeon's intent to the generator "G" for allocating the correct haptic response. In a first position, the lever 530, upon movement thereof, cooperates with the input to impart movement to the jaw members 42, 44 between the first and second positions with a closure pressure within the range of about 0.1 kg/cm$^2$ to about 2 kg/cm$^2$. Pressures up to and including the lower range of the below-identified sealing pressure range are also contemplated. In a second position, movement of the lever 530 imparts movement to the jaw members 42, 44 with a closure pressure within the range of about 3 kg/cm$^2$ to about 16 kg/cm$^2$.

Various safety measures may be employed using one or more mechanical, electromechanical or software that would only allow a sealing pressure to be delivered when energy is being applied. For example, a slight delay may be programmed into the control software to delay activation of electrosurgical energy until a proper jaw pressure is applied between the jaw members 42, 44 via the lever 530.

In another embodiment according to the present disclosure, one or more proximity sensors, cameras, or potentiometers (collectively referred to as "proximity devices" 760) may be employed to provide haptic feedback to the surgeon. One or more of these proximity devices 700 may be operably associated with any of the above-identified components of the instrument 10 or end effector assembly 40 and used to detect movement of a component relative to a fixed component or between two or more components. For example, a proximity device 760 may be disposed on one or both jaw members 42, 44 and configured to detect an aperture between the jaw members 42, 44 and provide feedback relating thereto to the robotic controller 505 or control device 504 for controlling the resistance of the lever 530. The proximity device 760 may also be placed relative to the spring 456 for the same or similar purpose.

Prior to actuation and/or during a homing step as described above, the proximity device 760 may be utilized to communicate a baseline measurement to the robotic controller 505 or control device 504. Once the lever 530 is actuated, any deviation from the baseline is measured and communicated to the robotic controller 505 or control device 504 for increasing or decreasing the resistance of the lever 530 to simulate haptic feedback. As mentioned above, switch 536 may be utilized to convey the surgeon's intent to the robotic controller 505 or control device 504 for allocating the correct haptic response. In a first position, the lever 530, upon movement thereof, cooperates with the input 140 to impart movement to the jaw members 42, 44 between the first and second positions with a closure pressure within the range of about 0.1 kg/cm$^2$ to about 2 kg/cm$^2$. Pressures up to and including the lower range of the below-identified sealing pressure range are also contemplated. In a second position, movement of the lever 530 imparts movement to the jaw members 42, 44 with a closure pressure within the range of about 3 Kg/cm$^2$ to about 16 Kg/cm$^2$.

It will be understood that various modifications may be made to the aspects and features disclosed herein. For example, a strain gauge or transducer may be disposed at a distal end of the wrist to provide feedback relating to the force input relating to the possible negative effects of articulation losses therefrom. It is also envisioned that strain gauges may be disposed on various locations on the instrument to measure various forces and provide feedback for particular purposes. Any and all known types of strain gauges are contemplated herein. Therefore, the above description should not be construed as limiting, but merely as exemplifications of various aspects and features. Those skilled in the art will envision other modifications within the scope and spirit of the claims appended thereto.

What is claimed is:

1. A robotic surgical system, comprising:

an electrosurgical instrument, including:

an instrument housing having a shaft extending therefrom;

an end effector assembly disposed at a distal end of the shaft, the end effector assembly including first and second jaw members, at least one of which is movable between a first position wherein the first and second jaw members are spaced relative to one another and a second position wherein the first and second jaw members cooperate to grasp tissue;

an input operably disposed within the instrument housing;

a jaw drive rod configured to move the jaw members between the first and second positions; and a force limiting assembly coupled between the jaw drive rod and the input and configured to regulate movement of the jaw drive rod in response to movement of the input;

a strain gauge operably coupled to the jaw drive rod and configured to measure an amount of strain indicative of a strain on the jaw drive rod and communicate the amount of strain to a robotic controller operably coupled to the input; and an operating console remotely disposed relative to the electrosurgical instrument, the operating console including:

at least one handle configured to communicate with the input for controlling the movement of the jaw members, the at least one handle including a housing having a lever operably coupled thereto and movable relative to the housing from an un-actuated position, wherein the lever is a first distance from the housing, to an actuated position, wherein the lever is a second distance from the housing that is less than the first distance, the housing including a cavity defined therein configured to house one or more components therein configured to operably connect to the input such that movement of the lever relative to the housing correlates to movement of the input, the one or more components configured to operably regulate a resistance of the lever to movement relative to the housing based upon the amount of strain from the strain gauge;

a switch movable between a first switch position and a second switch position; and the robotic controller, wherein the robotic controller is coupled to the switch and the at least one handle, the robotic controller configured to regulate the resistance of the lever based on the position of the switch, wherein, in the first switch position corresponding to a tissue manipulation and/or grasping mode of the electrosurgical instrument, the lever is movable from the un-actuated position to the actuated position and the resistance of the lever to movement from the un-actuated position to the actuated position is regulated based on a first strain curve defining a first relationship between the amount of strain and the resistance, and wherein, in the second switch position corresponding to a tissue treatment mode of the electrosurgical instrument for supplying electrosurgical energy to tissue, the lever is movable from the un-actuated position to the actuated position and the resistance of the lever to movement relative to the housing from the un-actuated position to the actuated position is regulated based on a second, different strain curve defining a second, different relationship between the amount of strain and the resistance.

2. The robotic surgical system according to claim 1, wherein at least one of the first strain curve or the second strain curve is based at least in part on a baseline strain measurement measured during manufacturing.

3. The robotic surgical system according to claim 1, wherein at least one of the first strain curve or the second strain curve.

4. The robotic surgical system according to claim 1, wherein at least one of the first strain curve or the second strain curve is non-linear.

5. The robotic surgical system according to claim 1, wherein the combination of components disposed in the cavity include levers, gears, linkages, and springs.

6. The robotic surgical system according to claim 1, wherein the tissue treatment mode of the electrosurgical instrument includes tissue sealing.

7. The robotic surgical system according to claim 1, wherein the first relationship is a first ratio of resistance to strain and wherein the second relationship is a second, different ratio of resistance to strain.

8. The robotic surgical system according to claim 1, wherein the switch is disposed on one of the at least one handle.

9. The robotic surgical system according to claim 1, wherein the switch is disposed on one of the at least one handle.

10. A robotic surgical system, comprising:

an electrosurgical instrument, including:

an instrument housing having a shaft extending therefrom;

an end effector assembly disposed at a distal end of the shaft, the end effector assembly including first and second jaw members, at least one of which is movable between a first position wherein the first and second jaw members are spaced relative to one another and a second position wherein the first and second jaw members cooperate to grasp tissue; and an input operably disposed within the instrument housing and operably coupled to a jaw drive rod configured to move the jaw members between the first and second positions;

a proximity device configured to detect a parameter indicative of a size of an aperture between the jaw members and to communicate the parameter to a robotic controller operably coupled to the input; and an operating console remotely disposed relative to the electrosurgical instrument, the operating console including:

at least one handle configured to communicate with the input for controlling the movement of the jaw members, the at least one handle including a housing having a lever operably coupled thereto and movable relative to the housing from an un-actuated position, wherein the lever is a first distance from the housing, to an actuated position, wherein the lever is a second distance from the housing that is less than the first distance, the housing including a cavity defined therein configured to house one or more components therein configured to operably connect to the input such that movement of the lever relative to the housing correlates to movement of the jaw members between the first and second positions, the one or more components configured to operably regulate a resistance of the lever to movement relative to the housing throughout the range of motion based upon the size of the aperture;

a switch movable between a first switch position and a second switch position; and the robotic controller, wherein the robotic controller is coupled to the switch and the at least one handle, the robotic controller configured to regulate the resistance of the lever based on the position of the switch, wherein, in the first switch position corresponding to a tissue manipulation and/or grasping mode of the electrosurgical instrument, the lever is movable from the un-actuated position to the actuated position and the resistance of the lever to movement relative to the housing from the un-actuated position to the actuated position is regulated based on a first curve defining a first relationship between the size of the aperture and the resistance, and wherein, in the second switch position corresponding to a tissue treatment mode of the electrosurgical instrument for supplying electrosurgical energy to tissue, the lever is movable from the un-actuated position to the actuated position and the resistance of the lever to movement relative to the housing from the un-actuated position to the actuated position is regulated based on a second, different curve defining a second, different relationship between the size of the aperture and the resistance.

11. The robotic surgical system according to claim 10, wherein the proximity device includes at least one of a proximity sensor, camera or potentiometer.

12. The robotic surgical system according to claim 10, wherein the proximity device is operably coupled to a spring and measures the size of the aperture based upon the movement of the spring.

13. The robotic surgical system according to claim 10, wherein the proximity device is operably coupled to at least one of the jaw members and measures the size of the aperture based upon the movement of the at least one jaw member.

14. The robotic surgical system according to claim 10, wherein the tissue treatment mode of the electrosurgical instrument includes tissue sealing.

15. The robotic surgical system according to claim 10, wherein the first relationship is a first ratio of resistance to aperture and wherein the second relationship is a second, different ratio of resistance to aperture.

* * * * *